United States Patent
Roy

[19]

[11] Patent Number: 6,135,110
[45] Date of Patent: Oct. 24, 2000

[54] TRACHEOSTOMY TUBE

[75] Inventor: Ronald R. Roy, Spofford, N.H.

[73] Assignee: Sims Portex Inc., Keene, N.H.

[21] Appl. No.: 09/063,897

[22] Filed: Apr. 22, 1998

[51] Int. Cl.$^7$ .................................................. A61M 16/00
[52] U.S. Cl. ............................ 128/207.15; 128/202.97; 128/207.14; 128/912
[58] Field of Search .................. 128/207.14, 207.15, 128/207.17, 200.26, 207.18, 207.29, 912, 202.27; 604/265, 264, 533, 534, 535, 536; 623/9

[56] References Cited

U.S. PATENT DOCUMENTS

| | | |
|---|---|---|
| 3,169,529 | 2/1965 | Koenig . |
| 3,556,103 | 1/1971 | Calhoun . |
| 3,659,612 | 5/1972 | Shiley et al. . |
| 3,688,774 | 9/1972 | Akiyama . |
| 3,693,624 | 9/1972 | Shiley et al. ............................ 128/351 |
| 3,696,624 | 10/1972 | Bennett . |
| 3,987,798 | 10/1976 | McGinnis . |
| 4,009,720 | 3/1977 | Crandall . |
| 4,029,105 | 6/1977 | Faust . |
| 4,064,882 | 12/1977 | Johnson et al. . |
| 4,235,229 | 11/1980 | Ranford et al. . |
| 4,315,505 | 2/1982 | Crandall et al. . |
| 4,449,523 | 5/1984 | Szachowicz et al. . |
| 4,852,565 | 8/1989 | Eisele . |
| 5,054,482 | 10/1991 | Bales . |
| 5,056,515 | 10/1991 | Abel . |
| 5,067,496 | 11/1991 | Eisele . |
| 5,318,021 | 6/1994 | Alessi . |
| 5,390,669 | 2/1995 | Stuart et al. . |
| 5,458,139 | 10/1995 | Pearl . |
| 5,460,176 | 10/1995 | Frigger ............................... 128/207.14 |
| 5,819,734 | 10/1998 | Deiley et al. ....................... 128/207.17 |

FOREIGN PATENT DOCUMENTS

| | | |
|---|---|---|
| 2 608 724 | 6/1988 | France . |
| 183904 | 7/1965 | U.S.S.R. . |

*Primary Examiner*—Aaron J. Lewis
*Assistant Examiner*—Joseph F. Weiss, Jr.
*Attorney, Agent, or Firm*—Louis Woo

[57] ABSTRACT

To ensure that the inner cannula is mated to the outer cannula of a tracheostomy tube, a pressure adjusting device is provided to the collar of the inner cannula so as to apply a biasing force against the tabs that extend from the hub of the outer cannula. The torque force that is required to assemble/disassemble the inner cannula to/from the outer cannula may be adjusted by increasing or decreasing the thickness of the pressure adjusting device which may be in the form of a spring ring which elasticity is adjustable by varying the thickness thereof. Ramps are provided within the collar of the inner cannula to guide the movement of the tabs relative to that of the collar. In addition, stops are provided within the collar for arresting any further movement of the tabs with respect to the collar. Indents are further provided within the collar whereat the tabs can rest. By thus applying a biasing force against the tabs while they rest on the indents, absent a deliberate disassemble torque to the collar, the inner cannula will stay securely fixed to the outer cannula.

12 Claims, 2 Drawing Sheets

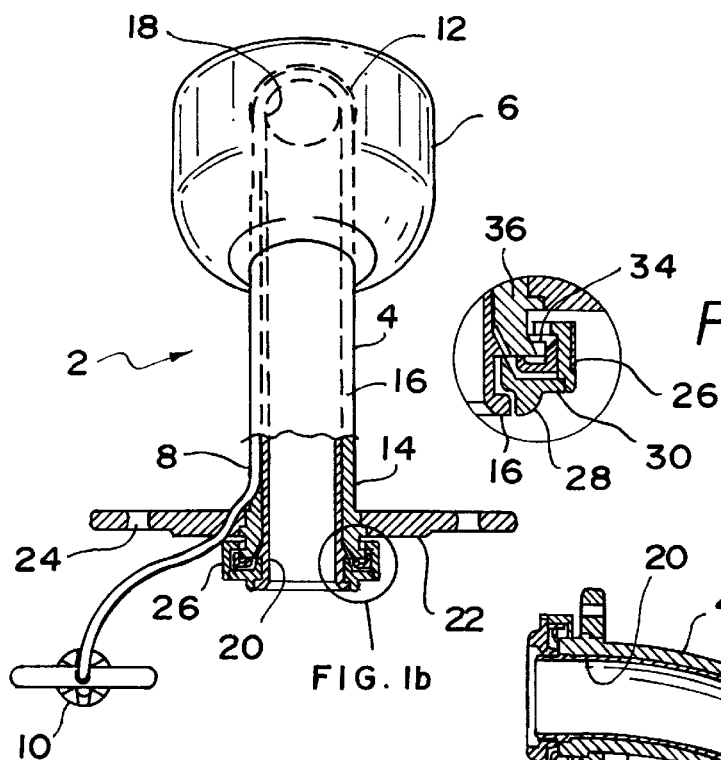
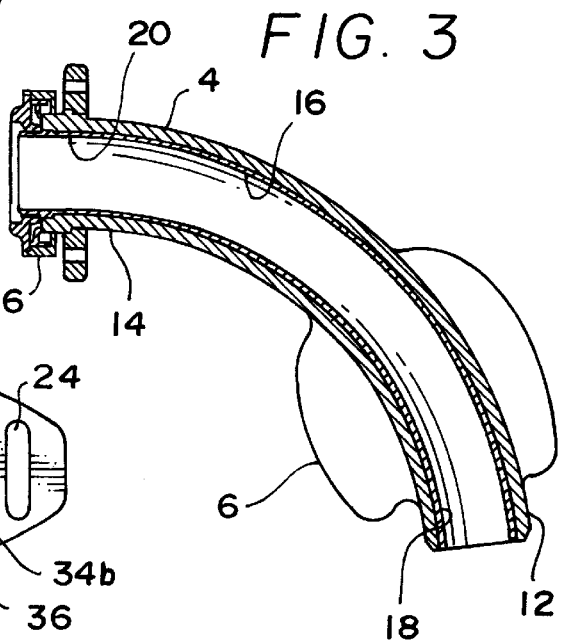
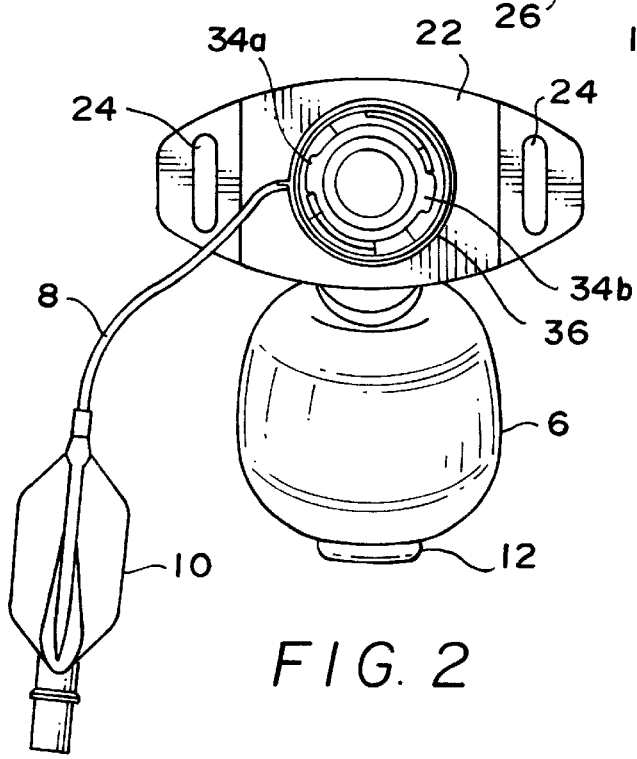

TRACHEOSTOMY TUBE

FIELD OF THE INVENTION

The present invention relates to tracheostomy tubes and particularly to a tracheostomy tube that has a component for adjusting the force required to assemble/disassemble the inner cannula to/from the outer cannula of the tracheostomy tube.

BACKGROUND OF THE INVENTION

Tracheostomy tubes are well known. They are used to provide direct access to a patient's trachea for either forced respiration or to provide an air passage for the patient.

A type of tracheostomy tube has an outer or exterior cannula into which an inner or interior cannula is inserted. By incorporating both an outer and an inner cannula, such tracheostomy tube enables only the removal of the inner cannula for cleaning without having to remove the outer cannula tube from the patient, thereby minimizing the discomfort to the patient and the need to remove the outer cannula once it is installed in the patient's trachea.

Given that the inner cannula has to be removed from the outer cannula for purposes such as for example cleaning, or for that matter different inner cannulas be used for the patient during different times of the day, the mating of the inner cannula to the outer cannula has to be done securely and, at the same time, the inner cannula has to be readily removable from the outer cannula.

One of the prior art tracheostomy tubes that has both an inner and outer cannula is the D.I.C.™ tracheostomy tube sold by the assignee of the instant invention. There, at least one circumferential extension is provided at the proximal end of the inner cannula so that when the inner cannula is pushed into the outer cannula, this circumferential extension comes to rest in a corresponding circumferential groove integrated to the hub of the outer cannula. It is in essence a kind of push and snap fit. However, an inadvertent movement on the part of the patient, or anyone else, could possibly cause the inner cannula to be pulled from the outer cannula.

Another tracheostomy tube secures the inner cannula to the outer cannula by providing a "twist-on lock" whereby, after the inner cannula is inserted into the outer cannula, a rotational movement of the hub of the inner cannula is effected relative to the hub of the outer cannula to secure the inner cannula to the outer cannula by means of the interaction between two bumps at the hub of the inner cannula with two internal grooves at the hub of the outer cannula. The problem with this tracheostomy tube is that since both the inner and outer cannulas are molded components, sometimes such components are not molded to exactly the correct specification. Thus, when the inner cannula, for example, is molded too thin, it can readily come loose from the outer cannula as for example when the patient coughs. On the other hand, if the inner cannula is molded too thick, the interaction between the bumps at the hub of the inner cannula and the internal grooves at the hub of the outer cannula may become somewhat tight so that when the medical personnel tries to mate the inner cannula to the outer cannula, her efforts to twist and lock the outer cannula into place with the inner cannula may cause undue discomfort to the patient.

A tracheostomy tube that provides for a secured engagement between its inner and outer cannulas, irrespective of the imperfection that may be due to the molding manufacturing process, is therefore needed. Moreover, the insertion of such tracheostomy tube to a patient should not cause a disproportionate amount of discomfort to the patient because the inner and outer cannulas may not have been produced exactly to specification.

SUMMARY OF THE INVENTION

The present invention tracheostomy tube comprises an outer cannula and an inner cannula each having a proximal end and a distal end. At the distal end of the outer cannula there is an inflatable cuff. There are two opposed tabs, integrated to the proximal end, or a hub thereat, of the outer cannula, extending away from each other. Each of these tabs may have an inclined edge and a protrusion or extension provided at the underside thereof. The inner cannula is of substantially the same length as the outer cannula, and is insertable therein or matable therewith. The distal end and proximal end of the inner cannula correspond respectively to the distal and proximal ends of the outer cannula. There is formed at the proximal end of the inner cannula a rotatable collar or ring. At the underside of the collar there are two opposed openings, each meant to mate with a corresponding one of the opposed tabs of the outer cannula. The underside of the collar further is configured to have an internal ramp extending from each of the openings to about a quarter turn of the collar. An indent is provided at the end of each of the internal ramps.

Of import to the instant invention tracheostomy tube is the fitting of a pressure adjusting mechanism such as a spring ring within the collar. This spring ring is an elastic ring that has an elasticity that can vary depending on the thickness or stiffness of the material of the ring. Thus, by inserting a spring ring with the appropriate thickness in the collar of an inner cannula, the torque force that is required to lock the inner cannula to the outer cannula can be adjusted to fit the type of inner cannula that is required for the patient for different occasions or for particular times of the day, such as for example during the patient's sleeping hours as compared to his waking hours, or ventilator-dependent as compared to spontaneous respiration.

In operation, once the distal portion of the outer cannula is positioned into the trachea of the patient and the outer cannula is fixedly anchored thereat as for example by means of a flange and the appropriate tie around the neck of the patient, the inner cannula is inserted to the outer cannula. At the end of the insertion, the collar about the proximal end, or hub, of the inner cannula is rotatably aligned so that the tabs at the outer cannula are inserted into the collar via the openings thereof. Thereafter, a clockwise rotational torque is applied to the collar. This causes the inner portion of the underside of the collar to interact with the tabs. After the collar is rotated a predetermined number of degrees, as for example a quarter turn, the tabs are positioned and come to rest at the corresponding indents formed at the underside of the collar. The spring ring provides a biasing force that keeps the tabs engaged to the corresponding indents of the collar. And depending on the thickness of the spring ring and the particular collar used, the amount of torque for assembling/disassembling the inner cannula to/from the outer cannula can be predetermined.

It is therefore an objective of the present invention to provide a tracheostomy tube that has a pressure adjusting mechanism for ensuring that the inner cannula is fixedly mated to the outer cannula, absent the deliberate application of a torque to the collar of the inner cannula for removing the same from the outer cannula.

It is yet another objective of the present invention to provide a tracheostomy tube having an outer cannula that is adaptable to be used with different inner cannulas that require different amounts of torque for assembly/disassembly from the outer cannula.

It is still another objective of the instant invention to provide a tracheostomy tube that has an outer cannula that is matable to different types of inner cannulas so that a patient can be fitted with different inner cannulas for different occasions or hours of the day.

BRIEF DESCRIPTION OF THE FIGURES

The above-mentioned objectives and advantages of the instant invention will become apparent and the invention itself will best be understood by reference to the following description of an embodiment of the instant invention taken in conjunction with the accompanying drawings, wherein:

FIG. 1a is a semi cut-away side view of a tracheostomy tube of the instant invention;

FIG. 1b is an enlarged view of a portion of the FIG. 1a tracheostomy tube;

FIG. 2 is a view of the FIG. 1a tracheostomy tube having been rotated 90 degrees in a direction toward the reader with the inner cannula removed;

FIG. 3 is a view of the FIG. 2 tracheostomy tube having been rotated 90 degrees to the right for illustrating the sectional view thereof;

DETAILED DESCRIPTION OF THE INVENTION

Figure 4A:
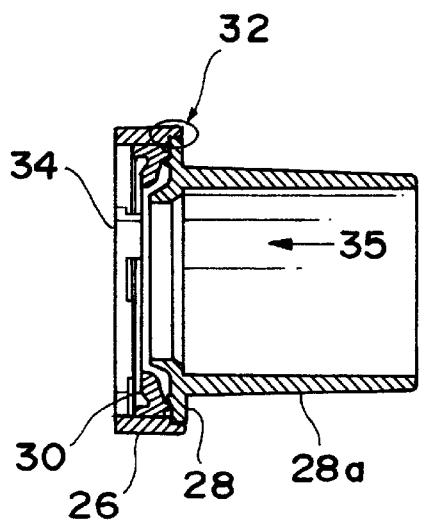
FIG. 4a is a cross-sectional view of an exemplar collar that is rotatably coupled to the proximal end of the inner cannula of the instant invention.

With reference to FIG. 1a, the instant invention tracheostomy tube 2 is shown to include an outer cannula 4 having attached thereto a balloon 6 that is inflatable in the trachea of a patient for preventing any leakage of air once outer cannula 4 is inserted to the trachea of the patient. An air line or tube 8 connected to a bulb 10 for providing air to inflate balloon 6 is also shown. Insofar as the way in which air is supplied to balloon 6 via tube 8 and bulb 10 is well known, no further discussion thereof is given herein.

As best shown in FIGS. 2 and 3, outer cannula 4 has a distal end 12 and a proximal end 14. Further shown in FIGS. 1a and 3 is an inner cannula 16 that is inserted or mated to outer cannula 4. Like outer cannula 4, inner cannula 16 has a distal end and a proximal end, designated in the drawings by 18 and 20, respectively. Further shown mounted about outer cannula 4 is a flange 22 that has a number of holes 24 by which tracheostomy tube 2 is fixedly mounted to a patient via a strap, not shown.

Figure 5A:
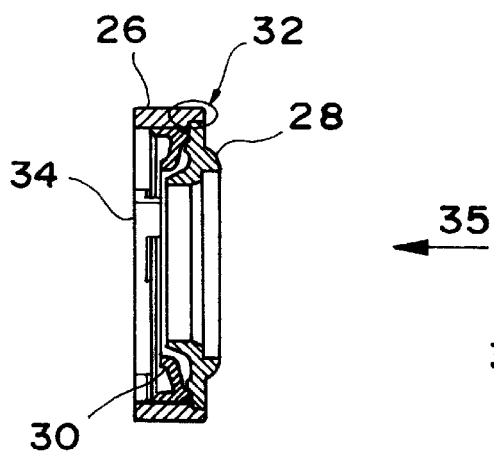
FIG. 5a is a low profile collar that is rotatably mounted to an end of the inner cannula of the instant invention.

As best shown in FIGS. 1a and 3, there is mounted to inner cannula 16 a collar 26 which cross-sectional view is amplified in FIG. 1b, and also FIGS. 4a and 5a. The same elements shown in FIGS. 1b, 4a and 5a are numbered the same. The same of course is true with respect to all of the other elements shown in FIGS. 1a, 2 and 3.

Figure 5B:
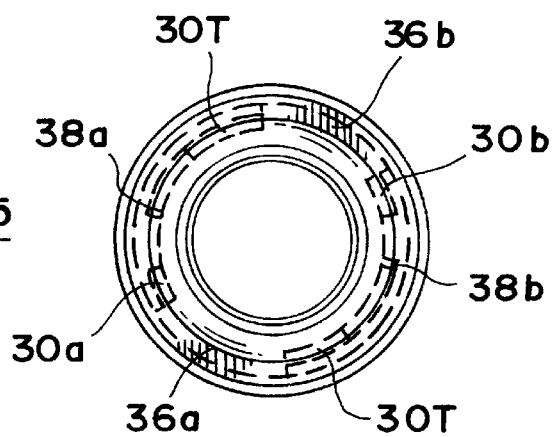
FIG. 5b is an end view of the FIG. 6a collar.

Returning to collar 26, and specifically the amplified view thereof in FIG. 1b and the cross-sectional views of FIGS. 4a and 5a, note that collar 26 has a main portion which, for the sake of convenience, is numbered 26 in FIG. 1b. Connected to portion 26 is a snap ring 28 which, together with portion 26, may be considered simply as the collar that is rotatably mounted about end 20 of inner cannula 16. Note that snap ring 28 is welded to collar 26, as illustrated by arrow 32 in FIGS. 4a and 5a. Fitted within collar 26 is a spring or elastic ring that has an elasticity that depends on its thickness or material. The thickness of spring ring 30 is dependent on the amount of torque or rotational force that is required to rotate collar 26 with respect to two tabs 34a and 34b, best shown in FIG. 2, extending from the proximal end, or a hub, of outer cannula 4. More on that later. For the time being, note that the thickness of spring ring 30 in the FIG. 4a collar is thicker than that shown in FIG. 5b.

Return to FIG. 2. There tabs 34 are shown to be mounted to a hub 36 which may be considered a part, or an extension, of proximal end 14 of outer cannula 4. One of tabs 34 is illustrated in FIG. 1b to be working cooperatively with collar 26 so as to be acted thereon by spring ring 30, which applied a biasing force against tab 34 at surface 36 thereof. Thus, depending on the thickness of ring 30, the torque required to overcome the biasing force applied by spring ring 30 against tabs 34 for rotating collar 26 relative to tab 34 would vary. This is illustrated more clearly in FIGS. 4a and 5a.

In FIG. 4a, a collar 28 having an extension 28a is shown. This extended collar may be used with an inner cannula for a patient during the patient's sleeping, ventilator assisted hours, as extension portion 28a may be connected to a breathing machine for helping the patient to breathe while the patient is in a sleep state. Although not shown in FIG. 4a, it should be appreciated that the proximal end 20 of the inner cannula 16 is mounted to end 34 of collar 28.

Figure 4B:
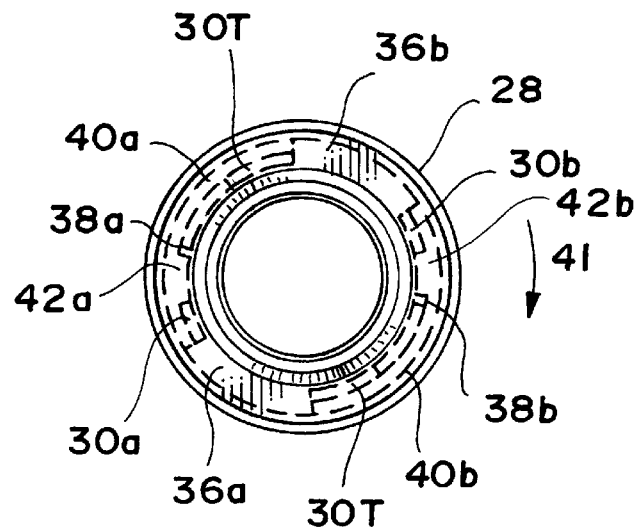
FIG. 4b is an end view of the FIG. 4a collar.

FIG. 4b is an end view of collar 28 in the direction of arrow 35. As shown, there are two opposed openings 36a and 36b for collar 26 that are meant to mate with tabs 34 or used thereby to enter into collar 26. As shown by the dotted lines, the portion of collar 26 which comes into contact with tabs 34 are ramps 30T. Also shown are two grooves 40a and 40b within collar 26 for guiding the movement of tabs 34 relative to collar 26, as collar 28 is turned in the direction indicated by rotational arrow 41. Further shown are two stops 30a and 30b within collar 26 at the end that prevent any further movement of tabs 34 relative to collar 26. Two indents 42a and 42b are provided before stops 30a and 30b, respectively, for mating with tabs 34a and 34b, or some extension protruding therefrom, so as to maintain tabs 34a and 34b in a "park or rest" position. When tabs 34 come to a rest state at indents 42, insofar as spring ring 30 applies a biasing force against tabs 34, collar 28 is ensured to be mated to hub 36 of outer cannula 4. And inasmuch as inner cannula 16 is rotatably coupled to collar 26, inner cannula 16 will remain fixedly mated to outer cannula 4 so long as no torque force is applied to collar 28 in a direction opposite to that of rotational arrow 41 to disassemble it from hub 36 of outer cannula 4. Such disassemble torque of course has to have a greater force than that of the biasing force being applied to tabs 34 by spring ring 30.

FIG. 5a illustrates a low profile collar 28 that is used with inner cannula 16 for providing a patient with a tracheostomy tube that the patient can wear during his waking or spontaneous respiration hours. Aside from the fact that collar 28 of the FIG. 5a embodiment does not have an extension connecting thereto, it operates the same way as the extended collar 28 shown in FIG. 4a, with the following one exception. That is, its spring ring 30 has a thickness that is less than the spring ring 30 for the FIG. 4a collar. This is because it has been determined that not as much torque is needed to assemble/disassemble the inner cannula to which the FIG. 5a collar 28 is mounted, as compared to the torque that is required to assemble/disassemble an inner cannula having the FIG. 4a collar attached thereto, to/from an outer cannula. To elaborate, the collar illustrated in FIG. 4a could be used for connecting the tracheostomy tube to a breathing machine while the patient is asleep. Since the patient is in the sleep state, it is desirable to require that a bigger torque force be needed to remove the inner cannula from the outer cannula of the tracheostomy tube, both as a safeguard to ensure that the patient is connected to a breathing device while he is asleep, and to prevent the inadvertent removal of the inner cannula from the outer cannula by the patient. The same scenario does not occur when the patient is in his waking state. Hence there is no need to require as great a torque force to assemble/disassemble the inner cannula to/from the outer cannula with the FIG. 5a collar.

In operation, once the inner cannula is inserted to the outer cannula and tabs 34 are aligned with openings 36, the user only needs to rotate collar 28 in the direction indicated by rotational arrow 41 to twist lock inner cannula 16 to outer cannula 4. To remove inner cannula 16 from outer cannula 4, a torque has to be applied to collar 28 in the opposite direction of directional arrow 41 with a greater force than the biasing force applied to tabs 34 by spring ring 30 in order to rotate collar 28 to realign tabs 34 with openings 36, before removing collar 28, and therefore inner cannula 16, from outer cannula 4.

It should be appreciated that the present invention is subject to many variations, modifications and changes in detail. Thus, it is the intention of the inventor that all matter described throughout this specification and shown in the accompanying drawings be interpreted as illustrative only and not in a limiting sense. Accordingly, it is intended that this invention be limited only by the spirit and scope of the hereto appended claims.

What is claimed is:

1. A tracheostomy tube comprising:
   an outer cannula having one end including at least one tab means extending therefrom;
   an inner cannula removably matable to said outer cannula having a first end;
   collar means rotatably coupled to said first end of said inner cannula, said first end of said inner cannula not extending beyond said collar means, said collar means having at least one opening to which said tab means can mate with said collar means when said inner cannula is mated to said outer cannula; and
   pressure means fitted within said collar means;
   wherein, after said inner cannula is mated to said outer cannula and said tab means mated to said collar means, and said collar means is rotated to move said opening away from said tab means, said outer and inner cannulas are ensured to remain fixedly mated to each other due to said pressure means effecting a biasing force against said tab means to thereby prevent inadvertent rotation of said collar means relative to said tab means.

2. The tracheostomy tube of claim 1, wherein said pressure means comprises an elastic ring mounted within said collar means having an elasticity that varies in proportion to its thickness so that the amount of torque force required to rotate said collar means relative to said tab means can be adjusted.

3. The tracheostomy tube of claim 1, wherein said collar means includes at least one internal guide means for guiding the relative movement between said collar means and said tab means and at least one stop for preventing further relative movement between said collar means and said tab means once said collar means has been rotated relative to said tab means a predetermined number of degrees.

4. The tracheostomy tube of claim 1, wherein said collar means further comprises:
   at least one detent working cooperatively with said tab means for maintaining said outer cannula in a fixed relationship with said inner cannula absent application of a torque force to rotate said collar means so as to move said tab means and said detent away from each other.

5. A tracheostomy tube comprising:
   an outer cannula having a hub including at least two opposed tabs extending therefrom;
   an inner cannula removably matable to said outer cannula, said inner cannula having a first end;
   a collar having at least two opposed openings to which said opposed tabs are inserted movably coupled to said hub of said outer cannula when said inner cannula is mated to said outer cannula, said collar being freely coupled to said first end of said inner cannula and forming a top for said outer cannula when said inner cannula is mated to said outer cannula; and
   an elastic ring fitted within said collar for applying a biasing force against said tabs when said collar is mated to said hub and rotated relative thereto to move said tabs within said collar away from said openings, said biasing force maintaining said tabs and therefore said hub in a position relatively fixed to said collar to thereby ensure that said inner cannula is securely mated to said outer cannula absent the application of a torque force for rotating said collar relative to said hub which is greater than said biasing force.

6. The tracheostomy tube of claim 5, wherein said elastic ring has an elasticity that varies in proportion to its thickness so that the amount of torque force required to rotate said collar relative to said hub varies as a function of said thickness.

7. The tracheostomy tube of claim 5, wherein said collar comprises at least two internal ramps each for guiding the movement of a corresponding one of said tabs within said collar, and at least one stop for preventing further movement of said tab relative to said collar when said collar has been rotated relative to said tab a predetermined number of degrees.

8. The tracheostomy tube of claim 5, wherein said collar further comprises at least two detents each working cooperatively with a corresponding one of said tabs for maintaining said outer cannula in a fixed relationship with said inner cannula once said tabs are moved into position relative to said detents.

9. A method of maintaining inner and outer cannulas fixedly positioned relative to each other in a tracheostomy tube, said tracheostomy tube including an outer cannula having a hub having at least one tab extending therefrom and an inner cannula removably matable to said outer cannula having a first end, said method comprising the steps of:
   rotatably coupling a collar to said first end of said inner cannula, said inner cannula not extending beyond said collar once said inner cannula is mated to said outer cannula;
   providing to said collar at least one opening to which said tab enters said collar when said inner cannula is mated to said outer cannula; and fitting an elastic ring within said collar for effecting a biasing force against said tab after said tab has entered into said collar and said collar being rotated to move said tab away from said opening, said biasing force causing said collar to remain in a position relatively fixed to said tab to thereby fixedly mate said inner and outer cannulas to each other absent any deliberate application of a torque force to rotate said collar relative to said tab.

10. The method of claim 9, further comprising the step of:

effecting said elastic ring to have an elasticity that varies in proportion to its thickness so that the amount of torque force required to rotate said collar relative to said tab is adjustable.

11. The method of claim 9, further comprising the steps of:

providing at least one ramp in said collar for guiding the movement of said tab in said collar; and providing a stop in said collar for preventing further movement of said tab within said collar once said collar has been rotated relative to said tab a predetermined number of degrees.

12. The method of claim 9, further comprising the steps of:

providing at least one detent in said collar to work cooperatively with said tab so that when said collar is rotated a predetermined number of degrees relative to said tab, said tab enters into a fixed relationship with said detent to lock said collar to said hub of said outer tube, said biasing force from said elastic ring acting against said tab to prevent said tab from moving away from said detent absent any deliberate attempt to apply a torque force to said collar to move said detent relative to said tab.

* * * * *